(12) United States Patent
Hille et al.

(10) Patent No.: US 6,814,976 B1
(45) Date of Patent: Nov. 9, 2004

(54) TRANSDERMAL THERAPEUTIC SYSTEM COMPRISING A RESERVOIR-TYPE PRESSURE-SENSITIVE ADHESIVE LAYER AND A BACK LAYER WITH UNI-DIRECTIONAL RESILIENCE

(75) Inventors: Thomas Hille, Neuwied (DE); Lothar Deurer, Koblenz (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 09/486,266

(22) PCT Filed: Aug. 21, 1998

(86) PCT No.: PCT/EP98/05321

§ 371 (c)(1),
(2), (4) Date: May 3, 2000

(87) PCT Pub. No.: WO99/12529

PCT Pub. Date: Mar. 18, 1999

(30) Foreign Application Priority Data

Sep. 5, 1997 (DE) .......................................... 197 38 855

(51) Int. Cl.[7] .......................... A61F 13/02; A61L 15/16; A63F 13/00
(52) U.S. Cl. ........................ 424/448; 424/449; 424/443
(58) Field of Search ................................ 424/448, 449, 424/443

(56) References Cited

U.S. PATENT DOCUMENTS

| | | | |
|---|---|---|---|
| 4,390,520 A | * | 6/1983 | Nagai et al. |
| 4,466,953 A | * | 8/1984 | Keith et al. |
| 4,780,168 A | | 10/1988 | Beisang et al. |
| 5,225,199 A | * | 7/1993 | Hidaka et al. |
| 5,240,711 A | * | 8/1993 | Hille et al. |
| 5,246,705 A | * | 9/1993 | Venkatraman et al. |
| 5,846,558 A | * | 12/1998 | Nielsen et al. |

FOREIGN PATENT DOCUMENTS

| | | | |
|---|---|---|---|
| DE | 166944 | * | 7/1971 |
| DE | 1 667 944 | | 7/1971 |
| DE | 27 33 549 C 2 | | 5/1986 |
| DE | 41 10 027 C2 | | 3/1991 |
| DE | 43 33 595 A 1 | | 4/1995 |
| DE | 44 23 850 A 1 | | 11/1996 |
| EP | 0 379 044 | | 7/1990 |
| EP | 0 430 019 B1 | | 11/1990 |
| WO | 41 10 027 C2 | | 3/1991 |
| WO | WO 92 17237 A | | 10/1992 |
| WO | WO 92/17237 | | 10/1992 |
| WO | 43 33 595 A | | 4/1995 |
| WO | 44 23 850 A | | 11/1996 |

* cited by examiner

Primary Examiner—Thurman K. Page
Assistant Examiner—Isis Ghali
(74) Attorney, Agent, or Firm—D. Peter Hochberg; Sean Mellino; Katherine R. Vieyra

(57) ABSTRACT

A transdermal therapeutic system (TTS), in particular a patch, is described, comprising:
- a detectable protective layer
- a pressure-sensitive adhesive reservoir layer and
- a backing layer with or without a coating of pressure-sensitive adhesive and featuring a unintentionally, preferably longitudinally, elastic material having an elasticity of at least 20%. The TTS is particularly suitable for use as a multi-day plaster, for the treatment, for instance, of pain or of drug dependency.

40 Claims, 1 Drawing Sheet

TRANSDERMAL THERAPEUTIC SYSTEM COMPRISING A RESERVOIR-TYPE PRESSURE-SENSITIVE ADHESIVE LAYER AND A BACK LAYER WITH UNI-DIRECTIONAL RESILIENCE

BACKGROUND OF THE INVENTION

1. Field of the Invention

The invention relates to a transdermal therapeutic system, in particular an active substance patch, comprising a detachable protective layer, a pressure-sensitive reservoir layer and a backing layer with or without a coating of pressure-sensitive adhesive. The invention also relates to a process for producing such a transdermal therapeutic system (occasionally abbreviated to TTS below) and to the use thereof.

2. Description of the Prior Art

A TTS is a skin-applied administration form for active substances for delivery through the skin, and has the appearance of traditional patches. It ought to be distinguished from a topical active substance plaster, for example, a rheumatism plaster or a corn plaster. A TTS of this kind can include one or more active substances which are delivered continuously over a fixed period at a predetermined rate to the site of application. ("Heilman Klaus: *Therapeutische Systeme—Konzept und Realisation programierter Arzneiverabreichung*" (*Therapeutic systems—Design and implementation of programmed drug administration*), $4^{th}$ edition, 1984, Ferdinand-Enke-Verlag, Stuttgart). The fixed period referred to above is usually 24 hours. For the treatment of chronic disorders, however, it is necessary to administer medicaments for a longer period. It may therefore be appropriate to apply a TTS for a period longer than 24 hours, since this is more likely to result in constant plasma levels.

A typical transdermal therapeutic system in the form of a patch is known from EP-B 0 430 019. It has a backing layer which is impermeable to the active substance, a pressure-sensitive adhesive reservoir layer, and a detachable protective layer. The active-substance-impermeable backing layer can be composed or flexible or inflexible material. Materials such as polymer films, metal foils, or a composite comprising a film which has been coated with aluminum by vapor deposition may be employed as the backing layer. Where such systems are worn on the skin for a prolonged period, in particular for treating chronic disorders, the relative rigidity of the TTS causes a pronounced sensation of a foreign body on the skin within a short period of time. This is extremely unpleasant for the user.

Another embodiment of such a TTS is described in U.S. Pat. No. 5,246,705. The transdermal system it describes has an elastomeric backing layer having a defined vapor transmission rate in the range from 0.1 to 20 $g/m^2/hr$ and a Young's modulus in the range of about $10^4$ to $10^9$ dynes/$cm^2$. Particularly, preferred materials for the elastomeric backing layer are, for example, A-B-A block copolymers, the A blocks comprising styrene and the B blocks comprising saturated hydrocarbon polymers such as, for instance, ethylene-butylene copolymers, ethylene-propylene copolymers, and the like. When the transdermal therapeutic systems as:per U.S. Pat. No. 5,246,705 are worn on the skin for a prolonged period, it is impossible to avoid the above-described sensation of a foreign body.

U.S. Pat. No. 4,780,168 discloses a strip-like wound bandage for sealing wounds, which is fabricated from a woven or non-woven polymer-based material having a planar stretching characteristic in the range from 0.5 to 110 (pounds/inch). Materials of such extensibility are, however, not immediately suitable as materials for backing layers of transdermal therapeutic systems. Either their extensibility is too low, in which case the aforementioned unpleasant foreign-body sensation is felt when the systems are worn on the skin for a prolonged period, or else they are much too extensible, in which case the production of transdermal therapeutic systems is accompanied by the curling effect, which is explained below.

During the production of the laminate from which the individual active substance patches are punched, the material for the backing layer comes under tensile stress and the resulting elastic return force means that, during punching, the opposite ends of the patches are each bent up. Because of the reject rate during the manufacturing process, the curling effect results in high costs, as well as unnecessary environmental burdens.

Aside from the abovementioned disadvantages, a material for the backing layer of a wound bandage is also unsuited to a TTS for other reasons, such as the required impermeability to the active substance.

The object of the invention is therefore to provide a transdermal therapeutic system which comprises a detachable protective layer, a pressure-sensitive adhesive reservoir layer and a backing layer with or without a coating of pressure-sensitive adhesive and which avoids the aforementioned disadvantages. In particular, there should be no sensation of a foreign body on the skin in the course of prolonged wearing, even for periods of from several days to about 1 or 2 weeks. Furthermore, the production of the TTS should not be accompanied by the curling effect, thus ensuring rational and inexpensive production.

This object is achieved in accordance with the invention by a transdermal therapeutic system, in particular an active substance patch, comprising a detachable protective layer, a pressure-sensitive adhesive reservoir layer and a backing layer with or without a coating of pressure-sensitive adhesive, the backing layer being a unidirectionally, especially longitudinally, elastic material having an elasticity of at least 20%.

Preferred embodiments of the TTS of the invention are the subject-matter of the dependent claims.

DETAILED DESCRIPTION OF THE INVENTION

Figure 1:
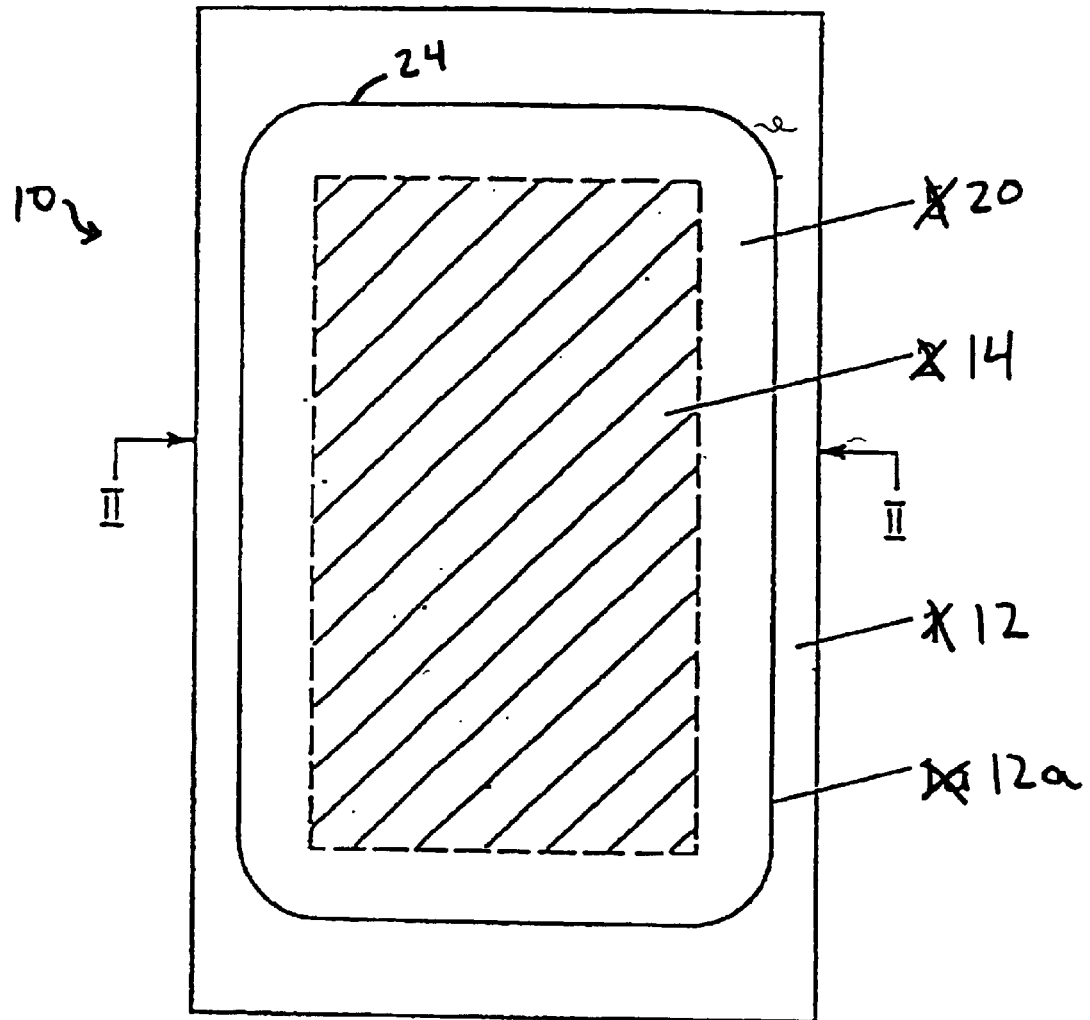
FIG. 1 is a plan view of the TTS of the invention according to the present invention.

In accordance with the invention, the TTS features not only a detachable protective layer and a pressure-sensitive adhesive layer but also a backing layer which, optionally, is coated with a pressure-sensitive adhesive and which has a specifically defined unidirectional elasticity. With regard to the TTS of the present invention, the elasticity is determined in accordance with the DIN standards 60 000 and 61 632 (April 1985), which are conventionally used for elasticity tests. Originally, these DIN standards applied to ideal bandages; however the horizontal force extension unit used to test the elasticity can be employed analogously for other materials as well. In accordance with the invention, the backing layer of the TTS is elastic in only one direction, i.e., in a longitudinal or a transverse direction. Relative to the longitudinal axis of the TTS, the transverse axis is that lying at a right angle to it. In a circular TTS, the longitudinal and transverse axis are of course identical in length. In particular, the backing layer material used in accordance with the invention is unidirectionally longitudinally elastic.

In the other direction, the backing layer is non-elastic. Non-elastic means that no elasticity can be found with testing by hand. In the case of measurements in accordance with DIN 61 632 the elasticity is less that 20%. In accordance wit the invention, therefore, the elasticity in one direction, mainly the elastic direction, is above 20%.

Since the production of the patch involves it being punched out from a laminate, it would also be possible to conceive in principle of the TTS being "unidirectionally" elastic at an angle to the longitudinal direction of the patch. Oblique elasticity of this kind is, however, the result of a superposition of elasticity in the transverse and longitudinal directions.

In the TTS of the present invention, the elasticity of the unintentionally elastic material used for the backing layer is preferably less than 150%. In a more preferred embodiment, the elasticity is in the range from 40% to 70%. The most preferred elasticity for a backing layer material, and, accordingly, that which is most advantageous for the achievement of the object on which the invention is based, lies within the range between 44% and 56%, always measured in accordance with DIN 61 632.

Preferred materials for the unidirectionally elastic backing layer are those which are microbially nondegradable. The material should be more than 90%, preferably more than 99%, microbially nondegradable. The degradability can be measured by conventional methods familiar to the person skilled in the art. Low degradability is particularly important in the case of TTSs which are to be worn on the skin for a prolonged period. The reason for this is that, owing to the transpiration of the skin, a microclimate in which bacteria, fungi, spores, etc. absolutely thrive develops directly below the section of skin covered by the TTS. Consequently, low microbial degradability, especially in the case of prolonged wearing, is extremely advantageous. The material of the backing layer can be a woven fabric, a nonwoven fabric, or a film. Where the backing layer comprises a polymer, the said polymer is selected advantageously from polyethylene, polypropylene, or polyesters, especially polyalkylene terephthalates.

A number of polymeric materials may be mentioned by way of example for the backing layer. Advantageous polymeric materials which meet the above requirement of low microbial degradability are polyterephthalic diesters obtainable by the reaction of a starting material selected from ethylene glycol, 1,4-butanediol, 1,4-dihydroxymethylcyclohexane, terephthalic acid, isophthalic acid, adipic acid, azelaic acid, sebacic acid, dimethyl terephthalate, dimethyl azelate, dimethyl sebacate, bisphenol A diglycidyl ether, n-decane-1, 10-dicarboxylic acid, polyethylene glycol and polybutylene glycol.

In the transdermal therapeutic system of the invention, it is likewise possible for a further separating layer to be arranged between the backing layer and the reservoir layer for the purpose, for example, of preventing active substance permeability. In this case, the backing layer on the skin-facing side, and/or the separating layer on the distal side, are/is likewise coated with pressure-sensitive adhesive.

For the effectiveness of a TTS of the invention, it is advantageous for the backing layer to project beyond the reservoir on all sides. This has the advantage that there are no losses of active substance in the lateral direction. Furthermore, the TTS of the invention can be produced in a particularly inexpensive manner since the sections containing active substance can be punched separately. This avoids expensive, environmentally harmful, leftover waste pieces containing active substance. The backing layer of the TTS has a water vapor permeability of at least 0.1 $g/m^2/h$, preferably from 1 to 20 $g/m^2/h$.

Where a woven or nonwoven fabric or else a porous film is used, the porosity lies within the range from 10% to 50%. Porosity here means the proportion of pores having an area of less that or equal to 400 $\mu m^2$ as a percentage of the reference area in question. This relative pore area can be determined by measuring and counting the pores of any unextended reference area under the microscope or a thread counter.

If a woven fabric is used for the transdermal therapeutic system (TTS) of the invention, the backing layer has a number of warp threads in the range of 300–350, preferably in the range of 310–330, and/or a number of weft threads in the range from 100, to 140, preferably in the range from 120 to 130, measured in each case per 10 cm of unextended fabric.

The pressure-sensitive adhesive reservoir layer of the transdermal therapeutic system of the invention comprises at least one active substance. This substance is preferably selected from the group consisting of psychopharmaceuticals, analgesics and hormones. Particular substances which may be considered include estradiol as a hormone and buprenorphine as an analgesic. The psychopharmaceutical is preferably a parasympathomimetic. Particularly suitable parasympathomimetics are the following:

1. choline esters, e.g. acetylcholine, bethanechol, carbachol, or methacholine;
2. alkaloids, e.g. arecoline and its derivatives, pilocarpine;
3. choline esterase inhibitors, e.g. demacarium bromide, distigmine bromide, neostigmine, physostigmine, pyridostigmine bromide, galanthamine.

These substances can of course be used in combinations with one another. The active substance content is particularly set so that when the plaster is removed a pulloff effect occurs. This effect is explained hereinbelow.

Where a TTS includes a backing layer of limited water vapor permeability, such as a PET film, the skin is unable to give off water vapor at the application site while the TTS is being worn. This water becomes incorporated in the skin. At the application site, therefore, the water content is higher than the physiobiological norm. A substance which is difficult for the skin to absorb (such as buprenorphine, for example) becomes incorporated into a deposit in the skin. When the TTS is pulled off, the skin gives off water vapor suddenly. As a result of removal of this water vapor, there is a sudden increase in the concentration of the medicament to above the saturation concentration, since solvent is removed. A stable state is reached by the rapid emptying of the skin deposit. Therefore, as a result of the TTS being pulled off, there is a rapid increase in the plasma concentration of the active substance. The utilization of the pulloff effect is preferred for better utilization of active substance. In accordance with the present invention, therefore, the concentration of the active substance is set such that the abovementioned pulloff effect comes about.

The absolute level of active substance for achieving the pulloff effect cannot generally be defined validly with precision. It varies from one active substance to another and also depends on the embodiment of the TTS. Setting of the level can, however, be undertaken by the person skilled in the art without undue burden by means of routine experiments. In the case of buprenorphine, the level is about 5–15% by weight.

The pressure-sensitive adhesive reservoir layer may also include a water-absorbing polymer. In one preferred embodiment, the water-absorbing polymer is a polyvinylpyrrolidone. The polyvinylpyrrolidone preferably has a molecular weight in the range from $1\times10^3$ to $2\times10^6$. Such polyvinylpyrrolidones include Kollidon®.

For special purposes, moreover, such as for use in hospitals with many patients or for use in double blind studies where TTS containing active substance are compared with placebo TTS, it is preferred for the side of the TTS that faces outwards, that is, away from the skin, to carry in the backing layer a marking/control element which is differentiated from the remaining area This element can differ from the remaining portion of the backing layer in its structure or in other properties, such as elasticity or porosity. By means of such a marking/control element the properties of the backing layer can be made different. For example, the elasticity of such an element can be greater than the elasticity of the remaining portion of the backing layer. If such a marking/control element is specifically incorporated in one portion of the backing layer, then its relative elasticity, where desired, is preferably within a range situated about 20% below or about 20% above the elasticity of the remaining portion of the backing layer.

The marking/control element can also serve to distinguish the individual TTSs from one another in terms of their active substance content. This is done preferably by means of colored marking, for example by means of a colored thread or stripe. This is particularly advantageous if the TTS has to be held ready in large quantities at different dosages at one location: for example, a hospital with large numbers of patients.

Because of its backing layer, the transdermal therapeutic system of the invention is particularly suitable for use as a multi-day plaster. The backing layer is tailored to this requirement. Thus it can be used in particular to treat chronic pain or else to treat drug dependency.

The TTS of the present invention is produced by means of conventional processes. In general, such a process comprises the steps of producing the individual TTSs by punching from a presupplied strip-like laminate comprising the unidirectionally elastic backing layer of the invention, an active substance layer and a detachable layer.

In one particularly preferred process for producing the TTS of the invention, the above steps are modified to the effect that, in a presupplied strip-like laminate having an optionally pressure-sensitive adhesive, unidirectionally elastic backing layer and a detachable protective layer, pressure-sensitive adhesive active substance reservoir sections are inserted in sequence in the longitudinal direction, and the backing layer is separated by punching. Lastly, the protective layer in the spaces between the active substance reservoir sections is separated. This specific process is highly advantageous from both economic and environmental standpoints. Indeed, the separate insertion of the active substance reservoir sections avoids the formation of waste comprising active substance (which is usually very expensive) and thus the need to dispose, again at a great expense of such waste A similar process is described in DE-B 41 10 027, which is expressly incorporated herein by reference.

The invention is elucidated below with reference to a drawing and an exemplary embodiment.

Referring now to FIG. 1, a plan view of a TTS of the present invention is shown and referred to generally at numeral 10. Lying atop the detachable protective layer 12 is the backing layer 20, which is coated with a pressure-sensitive adhesive devoid of active substance. For exemplary purposes, detachable protective layer 12 is shown as rectangular. The backing layer 20 has the form of a rectangle with rounded corners 24. The punching line 12a outlines the form of the backing layer 20. It extends outside the laminate comprising the reservoir 14 and, optionally, a barrier or separating layer 16. The course of the punching line 12a means that loss of active substance is avoided when the TTS 10 is punched out. Within the backing layer 20 it is possible to make out the contours of the reservoir 14 and of the optional barrier or separating layer 16.

In the TTS shown, with the unidirectionally elastic backing layer 20, the the backing layer 20 protrudes beyond the abovementioned laminate comprising the reservoir 14 on all sides. The reservoir 14 is preferably rectangular in form. The rectangular from is preferred since it prevents active substance loss when the reservoir is cut.

Figure 2:
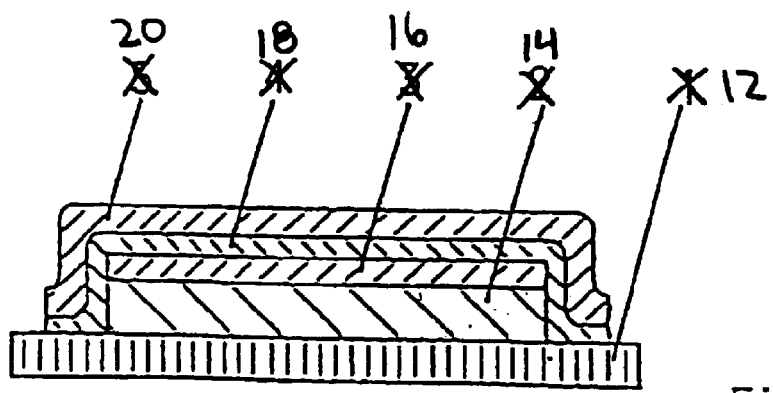
FIG. 2 is a cross section made through plane II—II of the TTS as shown in FIG. 1.

Referring now to FIG. 2, a cross section through plane II—II of FIG. 1 is shown. For clarity, the thickness of the layers have been exaggerated. The TTS 10 features the reservoir 14, the removable protective layer 12, the optional barrier layer 16, and a further layer 18 of pressure-sensitive adhesive devoid of active substance. This layer 18 is necessary when a barrier layer 16 is present. In this depicted embodiment, the backing layer 20 and the pressure-sensitive adhesive layer 18 devoid of active substance protrude beyond the abovementioned laminate on all sides.

EXAMPLES

In order to produce the unidirectionally elastic backing layer of the present invention, a woven polyester fabric having the following features was produced by means of the techniques known to the person skilled in the art.

| TEST FEATURES | UNIT | Nominal | MIN | MAX | $\overline{x}$ |
|---|---|---|---|---|---|
| WIDTH OF MATERIAL | mm | 1500 | 1300 | 1390 | 1360 |
| BASIS WEIGHT | $g/m^2$ | 100 | 95 | 103 | 100 |
| (unextended) | | | | | |
| (DIN 53854 + | | | | | |
| DIN 53884) | | | | | |
| EXTENSION | | | | | |
| (longitudinal) | % | — | — | — | — |
| (transverse) | % | 50 | 46 | 52 | 48 |
| (DIN 61632) | | | | | |
| NUMBER OF WARP | | 320 | 310 | 330 | 324 |
| THREADS | | | | | |
| Per 10 cm | | | | | |
| unextended | | | | | |
| NUMBER OF WEFT | | 125 | 124 | 126 | 124 |
| THREADS | | | | | |
| Per 10 cm | | | | | |
| unextended | | | | | |

In addition 49.175 kg of Durotak type 387–2054 (48.3% by weight solution), 4.450 kg of melted laevulinic acid, and 6.675 kg of oleyl oleate were homogenized with stirring. Then, 4.450 kg of Kollidon 90F were added in portions. Following dilution with 6.800 kg of ethanol, the mixture was stirred at 170–190 rpm for 5 hours. Then, 4.450 kg of buprenorphine base, suspended in 4.500 kg of ethyl acetate, was added. The mixture was diluted with 4.500 kg of ethyl acetate.

The mixture was stirred at 170 rpm for about 7 hours. It was then tested for homogeneity. When the composition was homogenous it was devolatilized, with the stirrer switched off.

Following homogenization, the adhesive composition was applied to a siliconized polyester film. The organic solvents were removed by drying at normally 35° C. to 80° C. The laminate, comprising siliconized polyester film and buprenorphine-containing pressure-sensitive adhesive layer, was subsequently covered with a second polyester film 23 µm thick.

The siliconized polyester film was removed from the resulting active substance laminate. Subsequently, rectangles measuring 50 cm$^2$ were punched out and were placed with their adhering face, at intervals of 3 cm, onto the siliconized fave of a further 100 µm polyester protective film. Atop these reservoir sections was placed the unidirectionally elastic, woven polyester fabric, which in this case was likewise coated with pressure-sensitive adhesive. Subsequently, individual longitudinally elastic patches were punched out. A wearing test was conducted on n=10 subjects using this TTS of the invention.

Comparative Example 1

In this example, a bidirectionally elastic woven polyester fabric was used instead of the unidirectionally elastic woven polyester fabric of the invention. The extensibility of this fabric (longitudinal and transverse extension) was 30% as measured in accordance with DIN 61 632. Its basis weight was 109 g/m$^2$. This material was a polyethylene terephthalate. In other respects, the TTSs produced in accordance with this comparative example were the same as those of the inventive example.

Using the TTSs according to this comparative example, a wear test was likewise conducted on n=10 subjects.

Comparative Example 2

TTSs were prepared in accordance with Example 1 and Comparative Example 1 but using a rigid polyester film (15 µm thick) of Hostaphan® RN 15, Hoechst AG, coated with pressure-sensitive adhesive, instead of a unidirectionally or bidirectionally elastic backing layer, respectively. In this case as well, a wear test was carried out with the resulting TTSs on n=10 subjects.

Evaluation

The comparative wear test of the TTSs of Example 1, Comparative Example 1 and Comparative Example 2 gave the following result.

When polyester film was used as the backing layer (Comparative Example 2), a sensation of a foreign body occurred on the very first day. On the second day, creasing occurred and, beginning on the third day, the TTS became detached. The TTS of Example 1 and that of Comparative Example 1 were torn without problems by all 10 subjects, with no sensation of a foreign body, with no impairment of bond strength, and, furthermore, with no skin irritations, for at least seven days. In respect of wear comfort, therefore, the TTS of Example 1 and that of Comparative Example 1 are approximately equal. However, with regard to the production of the TTS of Comparative Example 1, complications in production occurred in a frequency of more than 50%, these complications being attributable predominantly to the curling effect.

What is claimed is:

1. A transdermal therapeutic system comprising a detachable protective layer; a pressure-sensitive adhesive reservoir layer comprising at least one active substance; and a backing layer comprising unidirectional elastic material having an elasticity of at least 20%, wherein the material is a woven fabric, and wherein said reservoir layer contains a water-absorbing polymer.

2. The transdermal therapeutic system of claim 1 wherein the backing layer is a coating of pressure-sensitive adhesive.

3. The transdermal therapeutic system of claim 1 wherein the system is a patch.

4. The transdermal therapeutic system of claim 1 wherein the backing layer comprises longitudinally elastic material.

5. The transdermal therapeutic system of claim 1 wherein the elasticity of the backing layer is less than 150%.

6. The transdermal therapeutic system of claim 1 wherein the backing layer projects beyond the reservoir layer on all sides.

7. The transdermal therapeutic system of 2 further comprising a separating layer between the reservoir layer and the backing layer.

8. The transdermal therapeutic system of claim 1 wherein the elastic material of the backing layer has an elasticity of between 20–80%.

9. The transdermal therapeutic system of claim 8 wherein the elastic material of the backing layer has an elasticity of between 40–70%.

10. The transdermal therapeutic system of claim 9 wherein the elastic material of the backing layer has an elasticity of between 44–56%.

11. The transdermal therapeutic system of claim 1 wherein the material comprising the backing layer is more than 90% microbially nondegradable.

12. The transdermal therapeutic system of claim 11 wherein the material comprising the backing layer is more than 99% microbially nondegradable.

13. The transdermal therapeutic system of claim 1 wherein the backing layer comprises a material selected from the group consisting of a polyethylene, a polypropylene and a polyester.

14. The transdermal therapeutic system of claim 13 wherein the backing layer comprises a polyalkylene terephthalate.

15. The transdermal therapeutic system of claim 14 wherein the backing material is a polyterephthalic diester.

16. The transdermal therapeutic system of claim 15 wherein the backing material is a polyterephthalic acid diol ester obtainable by the reaction of a starting material selected from the group consisting of ethylene glycol, 1,4-butanediol, 1,4-dihydroxymethylcyclohexane, terephthalic acid, isophthalic acid, adipic acid, azelaic acid, sebacic acid, dimethyl terephthalate, dimethyl azelate, dimethyl sebacate, bisphenol A diglycidyl ether, n-decane-1, 10dicarboxylic acid, polyethylene glycol, and polybutylene glycol.

17. The transdermal therapeutic system of claim 1 wherein the reservoir layer comprises at least one active substance selected from the group consisting of a psychopharmaceutical, an analgesic and a hormone.

18. The transdermal therapeutic system of claim 1 wherein the water-absorbing polymer is a polyvinylpyrrolidone.

19. The transdermal therapeutic system of claim 18 wherein the polyvinylpyrrolidone has a molecular weight in the range of $1 \times 10^3$ to $2 \times 10^6$.

20. The transdermal therapeutic system of claim 1 wherein the backing layer facing outwardly has a differentiated marking element.

21. The transdermal therapeutic system of claim 20 wherein the marking element is a colored marking.

22. The transdermal therapeutic system of claim 21 wherein the colored marking is in strip form or a colored thread.

23. The transdermal therapeutic system of claim 20 wherein the marking element has an elasticity of between −20% to +20% relative to the elasticity of the remaining portion of the backing layer.

24. The transdermal therapeutic system of claim 1 wherein the backing layer has a water vapor permeability of at least 0.1 g/m²/h.

25. The transdermal therapeutic system of claim 24 wherein the backing layer, has a water vapor permeability of between 1 to 20 g/m2/h.

26. The transdermal therapeutic system of claim 1 wherein the backing layer has a number of warp threads in the range from 300 to 350 per 10 cm of unextended fabric.

27. A method of treating pain or drug dependency comprising administering an active substance in the transdermal therapeutic system of claim 1.

28. A method of treating pain or drug dependency comprising administering an active substance in the transdermal therapeutic system of claim 17.

29. A method of producing the transdermal therapeutic system of claim 1 comprising the steps of inserting pressure-sensitive adhesive substance reservoir sections in a sequence in a longitudinal direction into a presupplied strip-like laminate comprising a detachable protective layer and a backing layer comprising a unidirectional backing material; separating the backing layer by punching; removing the unwanted cut portion of the backing layers; and separating the protective layer in the space between the active substance reservoir sections.

30. The transdermal therapeutic system of claim 1 wherein the backing layer comprises a material selected from the group consisting of a woven fabric, a nonwoven fabric and a film.

31. The transdermal therapeutic system of claim 17 wherein the active ingredient is selected from the group consisting of oestriol, buprenorphine and a parasympathomimetic.

32. The transdermal therapeutic system of claim 31, wherein the parasympathomimetic active ingredient is selected from the group consisting of choline esters, alkaloids and choline esterase inhibitors.

33. The transdermal therapeutic system of claim 32, wherein the choline esters are selected from the group consisting of acetylcholine, bethanechol, carbachol and methacholine.

34. The transdermal therapeutic system of claim 32, wherein the alkaloids are selected from the group consisting of arecholine and its derivatives and pilocarpine.

35. The transdermal therapeutic system of claim 32, wherein the choline esterase inhibitors are selected from the group consisting of demacarium bromide, distigmine bromide, neostigmine, physostigmine, pyridostigmine bromide and galanthamine.

36. The transdermal therapeutic system of claim 32 wherein the parasympathomimetic active ingredients are used in combination with each other.

37. The transdermal therapeutic system of claim 30 wherein the fabric or film comprises pores having a size less than or equal to 400 μm² embracing an areal proportion of between 10% and 50% of said fabric or film.

38. The transdermal therapeutic system of claim 30 wherein the fabric has a number of warp threads in the range of 300 to 350 per cm of unextended fabric and a number of weft threads in the range from 100 to 140 per 10 cm of unextended fabric.

39. The transdermal therapeutic system of claim 38 wherein the number of weft threads is in the range from 120 to 130.

40. A method of treating pain or drug dependency comprising administering an active substance in the transdermal therapeutic system of claim 31.

* * * * *